United States Patent [19]
Yaginuma

[11] Patent Number: 5,652,432
[45] Date of Patent: Jul. 29, 1997

[54] CYLINDRICAL BODY INSPECTION APPARATUS UTILIZING DISPLACEMENT INFORMATION AND REFLECTED LIGHT INFORMATION

[75] Inventor: Yoshitaka Yaginuma, Naka-gun, Japan

[73] Assignee: Mitsubishi Nuclear Fuel Co., Tokyo, Japan

[21] Appl. No.: 468,756

[22] Filed: Jun. 6, 1995

[30] Foreign Application Priority Data

Jun. 28, 1994 [JP] Japan .................................. 6-146808

[51] Int. Cl.$^6$ .............................. G21C 3/00; G01N 21/00
[52] U.S. Cl. .............................. 250/559.06; 250/559.23; 250/559.42; 250/559.45; 250/226; 356/376; 356/356; 209/587; 209/579; 209/580
[58] Field of Search ........................ 250/559.06, 559.05, 250/559.07, 559.08, 559.19, 559.2, 559.22, 559.23, 559.24, 559.45, 559.42, 559.46, 559.48, 559.49, 226; 356/376, 386, 387, 398, 356; 209/576, 577, 579, 580, 581, 582, 587; 376/248, 261

[56] References Cited

U.S. PATENT DOCUMENTS

| | | | |
|---|---|---|---|
| 4,143,770 | 3/1979 | Grimmell et al. | 250/226 |
| 4,377,238 | 3/1983 | Wilks et al. | 250/223 R |
| 4,982,103 | 1/1991 | Meiffren et al. | 250/559.14 |
| 5,012,116 | 4/1991 | Russell | 250/559.46 |
| 5,147,047 | 9/1992 | Ahmed et al. | 209/538 |
| 5,186,887 | 2/1993 | Yaginuma | 376/248 |
| 5,379,329 | 1/1995 | Yaginuma et al. | 376/248 |

FOREIGN PATENT DOCUMENTS

| | | |
|---|---|---|
| 0 048 072 | 3/1982 | European Pat. Off. . |
| 0 583 092 | 2/1994 | European Pat. Off. . |
| 0 588 624 | 3/1994 | European Pat. Off. . |
| 0 593 156 | 4/1994 | European Pat. Off. . |
| 2 337 882 | 8/1977 | France . |
| 56-29147 | 3/1981 | Japan . |
| 60-209151 | 10/1985 | Japan . |
| 63-193040 | 8/1988 | Japan . |
| 3-226696 | 10/1991 | Japan . |

OTHER PUBLICATIONS

Patent Abstracts of Japan, vol. 18, No. 281 (P-1744), May 27, 1994, Derwent Abstracts, AN-94-104046, JP-A-6 051091, Feb. 25, 1994.
Patent Abstracts of Japan, vol. 16, No. 5 (P-1295), Jan. 8, 1992, Derwent Abstracts, AN-91-336561, JP-A-3 226696, Jul. 10, 1991.
Patent Abstracts of Japan, vol. 10, No. 72 (P-438), Mar. 22, 1986, JP-A-60 210745, Oct. 23, 1985.
Patent Abstracts of Japan, vol. 11, No. 370 (P-642), Dec. 12, 1987, Derwent Abstracts, AN 87-211411, JP-A-62 140053, Jun. 23, 1987.

(List continued on next page.)

*Primary Examiner*—Edward P. Westin
*Assistant Examiner*—John R. Lee
*Attorney, Agent, or Firm*—Oblon, Spivak, McClelland, Maier & Neustadt, P.C.

[57] ABSTRACT

The present invention relates to a cylindrical body inspection apparatus characterized in comprising: a) rotating mechanism for supporting and rotating a cylindrical body; b) sensor comprising a light emitting unit for irradiating light onto a surface to be inspected of a cylindrical body, and a light detecting unit for detecting incoming light reflected from the surface to be inspected; this sensor detects displacement information corresponding to a displacement of distance from the surface to be inspected to the light detecting unit, and information regarding the quantity of incoming light corresponding to quantity of reflected light from the surface to be inspected; c) computing unit for computing surface information and external form formation based on the above displacement information and information regarding quantity of incoming light from the sensor; and d) discriminating unit for discriminating the presence or absence of defects relating to shape of the cylindrical body based on the surface information and external form information obtained by means of the computing unit.

11 Claims, 9 Drawing Sheets

OTHER PUBLICATIONS

Patent Abstracts of Japan, vol. 13, No. 480 (P–952), Oct. 31, 1989, JP–A–1 191043, Aug. 1, 1989.

Patent Abstracts of Japan, vol. 13, No. 358 (P–916), Aug. 10, 1989, Derwent Abstracts, AN–89–182076, JP–A–1 119744, May 11, 1989.

Database WPI, Derwent Publications, AN–86–301782, JP–A–61 223588, Oct. 4, 1986.

CYLINDRICAL BODY INSPECTION APPARATUS UTILIZING DISPLACEMENT INFORMATION AND REFLECTED LIGHT INFORMATION

BACKGROUND OF THE INVENTION

1. Field of the Invention

The present invention relates to an inspection apparatus for detecting the presence/absence of defects such as abnormalities in the external shape, surface discoloration, density abnormalities, and the like, with regard to a cylindrical body such as a nuclear fuel pellet (hereinafter referred to as "pellet") and the like.

2. Background Art

Conventionally, a pellet to be loaded in a fuel rod is manufactured by means of forming nuclear fuel powder such as uranium dioxide or the like into a cylindrical green compact and sintering this green compact. With regard to this type of pellet, defects such as cracks and chips sometimes occur at the peripheral surface and/or opposite end faces during the manufacturing process; the pellet with these defects must be removed from the manufacturing process as a defective product. For this reason, a product pellet inspection apparatus is normally provided in the pellet manufacturing process.

An example of this type of pellet inspection apparatus is disclosed in Japanese Patent Application, First Publication, Laid-Open No. Hei 6-66990 by the inventors of the present invention. With regard to this inspection apparatus, a pellet which is ground to predetermined dimensions is transported to a pellet-drying/directional converter, and after drying end faces and the external circumferential surface therein, is inspected by the pellet inspection apparatus, and defective one is removed therefrom. Following inspection for surface defects by means of the aforementioned inspection apparatus, the pellet is further checked by visual inspection by a worker, and only the product free of defects is stored in a tray storage rack.

In the aforementioned pellet inspection apparatus, an image of the circumferential surface of the pellet is picked up by a circumferential surface inspection mechanism, such as a camera or the like, while rotating the pellet. Images of both end faces of the pellet are also picked up by an end face inspection mechanism. The above picked-up image data are then, for example, binary digitized by an image processing mechanism to determine the presence or absence of defects. In other words, in the case when defects such as pits, cracks, chips, dust adhesion, or the like are present on the circumferential surface and/or end faces of the pellet, the quantity of light reflected from these defective portions is less than the quantity of light reflected from surfaces free of defects, and thus it is possible to detect the presence or absence of such defects by means of the aforementioned image data processing.

However, when conducting visual inspection of pellet P using the aforementioned inspection apparatus, if the pellet is formed from a substance exhibiting a low reflectivity, it becomes very difficult to detect the aforementioned defects. For example, when the object to undergo inspection is a Gd pellet (gadolinium-containing uranium dioxide pellet), MOX pellet (uranium dioxide-plutonium dioxide mixed pellet) or the like, the S/N ratio of the pellet reflectivity with respect to the illumination light from the illuminating light source is poor. As a result, even when the surface to be inspected of the pellet is a normal surface free of defects, or alternatively, even when the surface to be inspected is defective, i.e., possessing cracks, chips and the like, a clear difference is not generated in the quantity of light received. Consequently, when attempting to detect the presence or absence of defects based on surface image data taken by a camera from a pellet exhibiting a poor S/N ratio of reflectivity with respect to the illuminating light, the gray level difference between the image data of normal surfaces and that of defective surfaces is small. As a result, misdetection occurs frequently, such that highly precise discrimination of defective pellets is not possible.

In addition, in order to precisely measure the volume and density of the pellet, measurement of the pellet dimensions is also performed. However, conventionally, in order to measure the pellet dimensions, it is necessary to first conduct sampling of the pellet and measure the pellet in an off-line manner. As a result, it is very difficult to conduct these measurements within a short period of time, and it is not possible to measure the entire quantity of pellets. In particular, in the case of a low-density pellet such as an MOX pellet, in addition to the inspection for surface defects, confirmation of the pellet density poses extreme importance; hence, there exists a strong demand for an apparatus which enables 100% inspection of pellets for density abnormalities at a high speed.

SUMMARY OF THE INVENTION

In consideration of the aforementioned circumstances, it is an object of the present invention to provide an inspection apparatus which is capable of determining the presence or absence of surface defects with high precision, even in the case of a cylindrical body having low S/N ratio of light reflectivity.

Another object of the present invention is to provide an inspection apparatus which is capable of measuring at a high speed the volume for use in detecting density abnormalities for the entire quantity of objects to be inspected, besides the inspection for surface defects of the cylindrical body.

In order to achieve these aforementioned objects, the present invention provides a cylindrical body inspection apparatus characterized in comprising: rollers for supporting and rotating the cylindrical body; a sensor comprising a light emitter for irradiating light onto a surface to be inspected of the cylindrical body, and a light detector for detecting incoming light reflected from the surface to be inspected; the sensor for detecting displacement information corresponding to a displacement of distance from the surface to be inspected to the light detector, and information regarding quantity of incoming light corresponding to a quantity of reflected light from the surface to be inspected; a computer for computing out surface information and shape information based on the displacement information and the information regarding quantity of incoming light; and a discriminator for discriminating the presence of surface defects of the cylindrical body based on the surface information and the shape information obtained by the computer.

According to the cylindrical body inspection apparatus of the present invention, the circumferential surface of the cylindrical body transported from the previous process is supported by the rollers; the displacement information and information regarding quantity of incoming light are detected by irradiating light from the sensor onto the surface to be inspected of the cylindrical body while rotating the cylindrical body. The detected displacement information and information regarding quantity of incoming light are then transmitted to the computer, where the surface information and external form information are computed out. The surface information and external form information obtained are then transmitted to a discriminator which compares the aforementioned information with a predetermined virtual standard surface, and in the case when a portion exhibiting a local displacement of distance and a characteristic fluctuation of a quantity of incoming light are present, the discriminator judges that a defect exits and thus discriminates between the presence or absence of defects of the cylindrical body.

The above-described sensors may be disposed respectively confronting both end faces and the circumferential surface of the cylindrical body. In such a case, it is possible to inspect the entire external surface of the cylindrical body comprising both end faces and the circumferential surface.

The aforementioned sensor may be a spot-type laser displacement sensor which may provide a position sensitive detector as a light detector, and for which a scanner is further provided for conducting reciprocal scanning in a direction intersecting a direction of rotation of the cylindrical body. Thus, the displacement information and information regarding quantity of incoming light of the end faces and circumferential surface are obtained.

In addition, the rotational information of the cylindrical body from the rollers, and positional information from the spot-type laser displacement sensor is input into the computer; the computer may compute out the surface information and the external form information out of the displacement information and the information regarding quantity of incoming light developed on the basis of the rotational information and the positional information.

The sensor may be a line-type laser displacement sensor that can irradiate a line-focused light beam across an entire length of the surface to be inspected of the cylindrical body. In such a case, it is possible to inspect the entire length of the surface to be inspected of the cylindrical body without conducting a reciprocal scan of the sensor. The line sensor may provide a plurality of position sensitive detectors or a 2-dimensional CCD as the light detector of the sensor.

The cylindrical body inspection apparatus of the present invention also provide an end face positioning mechanism for bringing an end face of the cylindrical body into a close contact with a positioning surface in a rotatable manner, and a circumferential surface positioning mechanism for bringing the circumferential surface of the cylindrical body into a close contact with a positioning surface in a rotatable manner. In such a case, an end face of the cylindrical body is brought into a close contact with a positioning surface by means of the end face positioning mechanism to position both end faces; and the circumferential surface of the cylindrical body is brought into a close contact with the rollers as a circumferential surface positioner.

In addition, the cylindrical body inspection apparatus according to the present invention may further comprise: a pickup apparatus for picking up color images of both the end faces and the circumferential surface of the cylindrical body; a computer for computing a degree of discoloration of a surface of the cylindrical body based on the color images; and a discoloration discriminator for discriminating the presence or absence of discoloration abnormalities on the cylindrical body based on the discoloration information.

The cylindrical body inspection apparatus according to the present invention may also comprise: a sensor comprising a light emitter for irradiating light onto a surface to be inspected of fine cylindrical body, and a light detector for detecting incoming light reflected from the surface to be inspected; the sensor for detecting displacement information corresponding to a displacement of distance from the surface to be inspected to the light detector, and information regarding quantity of incoming light corresponding to a quantity of reflected light from the surface to be inspected; a weigher for measuring the weight of the cylindrical body; a computer for computing out surface information, external form information based on the displacement information and the information regarding quantity of incoming light from the sensor, and for computing out volumetric information of the cylindrical body, from the volumetric information and weight information of the cylindrical body obtained by means of the weigher, the computer computing out density information of the cylindrical body; and a discriminator for discriminating the presence or absence of density abnormalities of the cylindrical body based on the density information computed by the computer.

In this case, the volume of the cylindrical body is computed from the surface information and external form information of the cylindrical body obtained by means of the computer. Furthermore, the density information is obtained from the weight information of the cylindrical body from the weigher, and the volumetric information. In this manner, it is possible to rapidly and precisely inspect the entire quantity of objects to be inspected for defects and density abnormalities of the external shape of the cylindrical body from the surface information, external form information, the density information and weight information of the cylindrical body. Subsequently, it is possible to determine the overall quality (i.e., pass/reject) of the cylindrical body based on an optional standard.

DETAILED DESCRIPTION OF THE PREFERRED EMBODIMENTS

In the following, a first embodiment of the present invention will be explained with reference to FIGS. 1~10.

Figure 1:
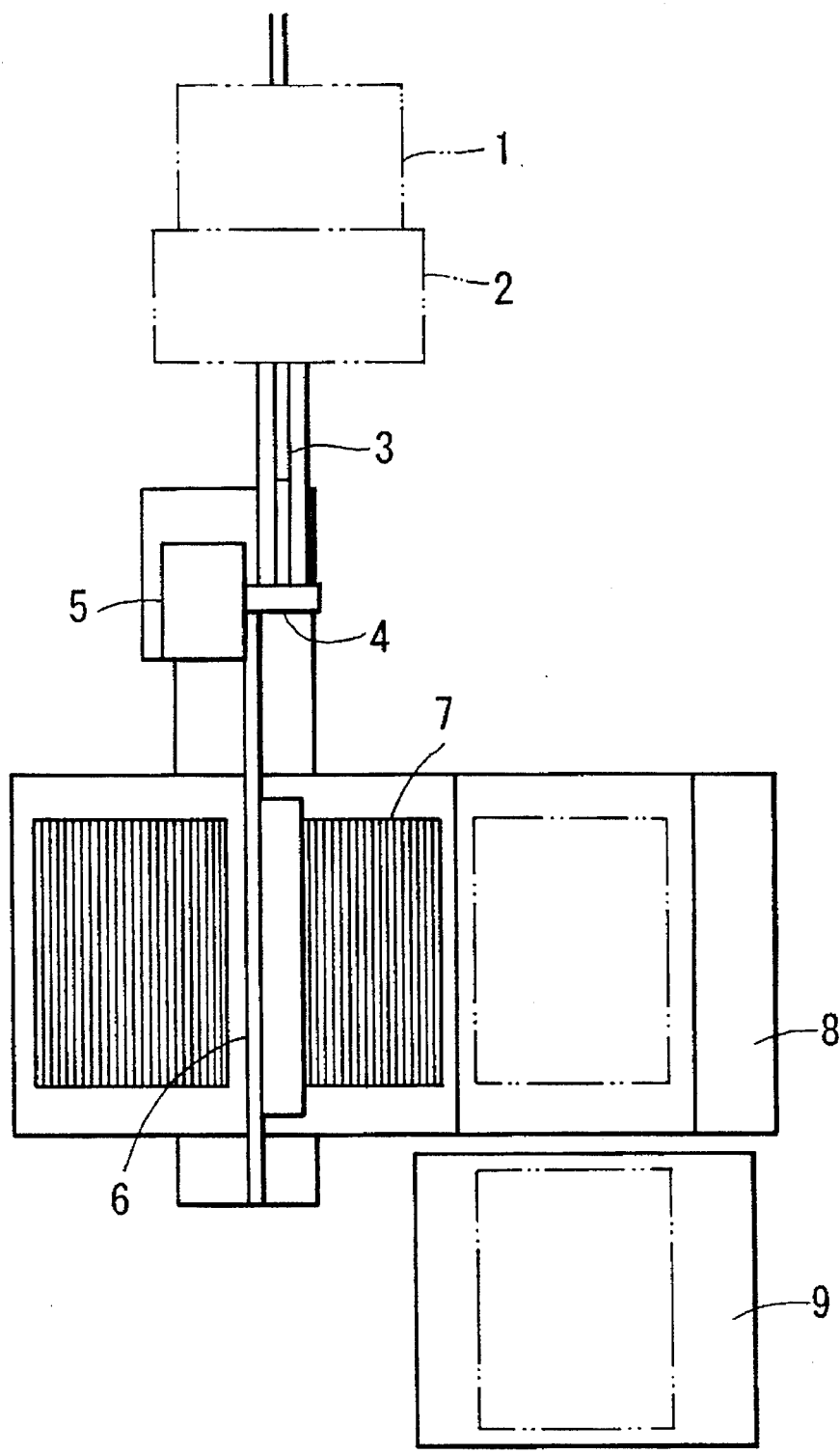
FIG. 1 is a plan showing an arrangement of an integrated pellet inspection apparatus.

FIG. 1 shows a structural outline of an integrated pellet inspection apparatus equipped with an inspection apparatus according to the first embodiment of the present invention. In this apparatus, a wet-type grinder 2 is connected to pellet-supplying mechanism 1 which supplies a cylindrically-shaped sintered pellet; the pellet is ground into a cylindrical body of predetermined dimensions by means of the aforementioned wet-type grinder 2. After the ground pellet is transported to pellet-drying/directional converter 4 along transport route 3 and dried therein, external inspection of the pellet is conducted by means of pellet inspection apparatus 5, and the defective products are removed.

Pellets passing through this external inspection are then collected by means of defect-free pellet collection unit 6, and after being checked by means of observation by a worker at the observation check section 7, the defect-free pellets are stored in tray storage rack 9 (stacker) by means of tray storing mechanism 8.

Figure 2:
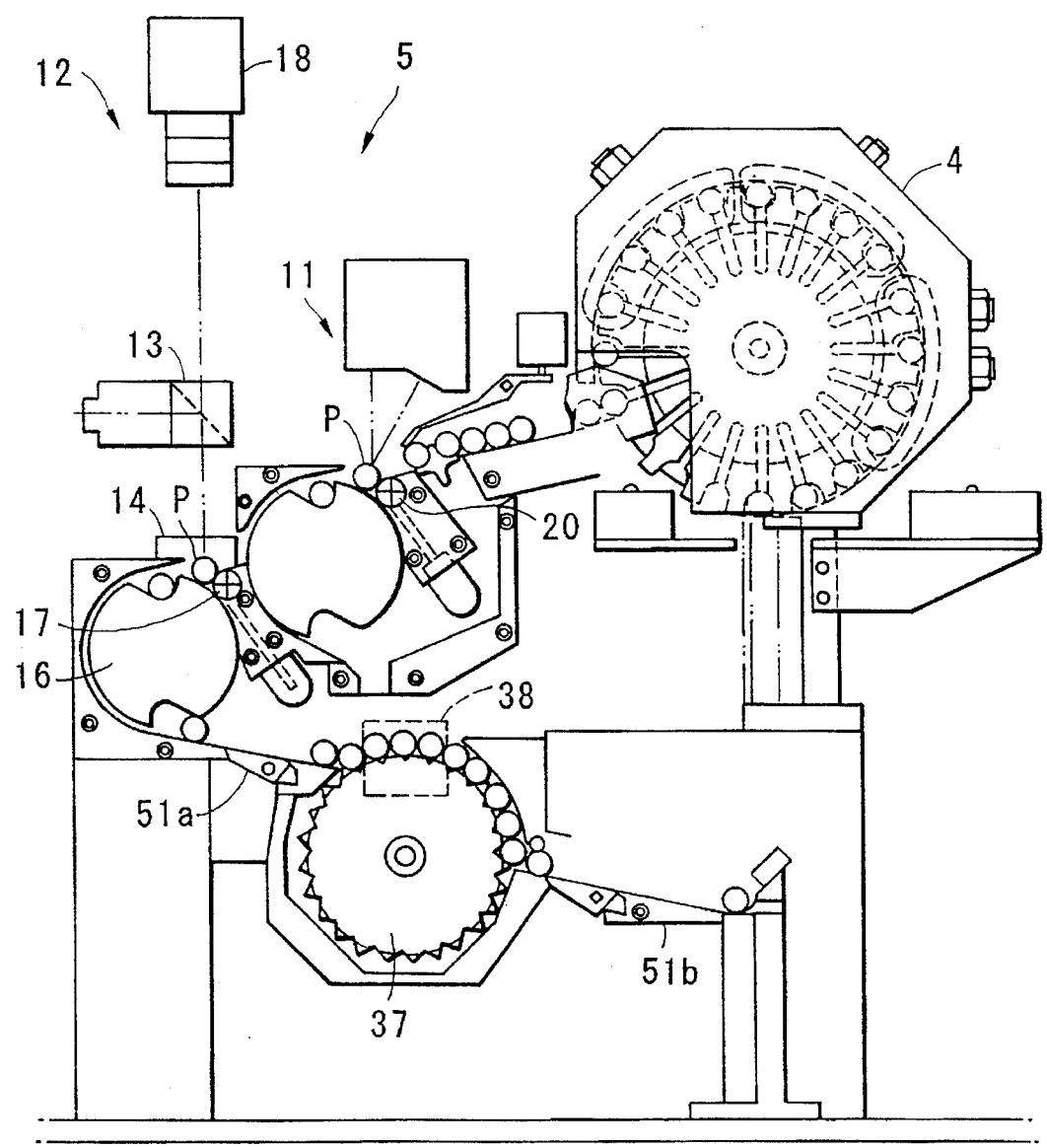
FIG. 2 is a front view showing an inspection apparatus according to a first embodiment of the present invention in the integrated pellet inspection apparatus shown in FIG. 1.

FIG. 2 shows a structural outline of pellet-drying/directional converter 4 and pellet inspection apparatus 5.

Pellet inspection apparatus 5 is provided above the transport route over which pellet P is transported in a radial direction from pellet-drying/directional converter 4. Pellet inspection apparatus 5 comprises pellet shape inspection unit 11 and external surface image inspection unit 12 which are arranged in the order of pellet P advancement.

Figure 3:
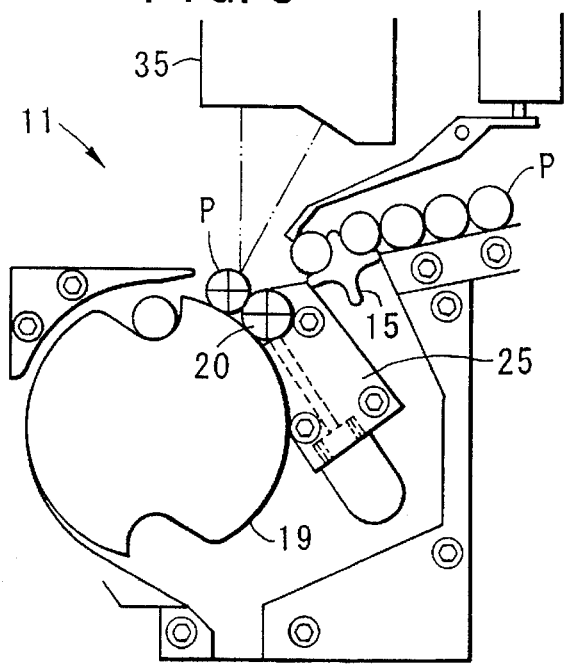
FIG. 3 is a front view of the pellet shape inspection trait according to the first embodiment from an axial direction of the pellet.

In the pellet shape inspection unit 11 shown in FIG. 3, an intermittent pellet supply mechanism 15 is provided for transporting intermittently pellet P sent from pellet-drying/directional converter 4. By means of the aforementioned intermittent pellet supply mechanism 15, pellet P is intermittently supplied between and supported on a first large diameter roller 19 and a first small diameter roller 20 wherein the former is provided behind the latter. Pellet P is rotated in compliance with the rotation of rollers 19 and 20 which, in turn, are interlocked and rotated with a predetermined peripheral speed of rotation by means of a driving motor 20a (see FIG. 8), and the rotational data as to peripheral displacement of the rollers are then transmitted to a control unit (to be explained hereinafter) as the rotational information of pellet P.

Figure 4:
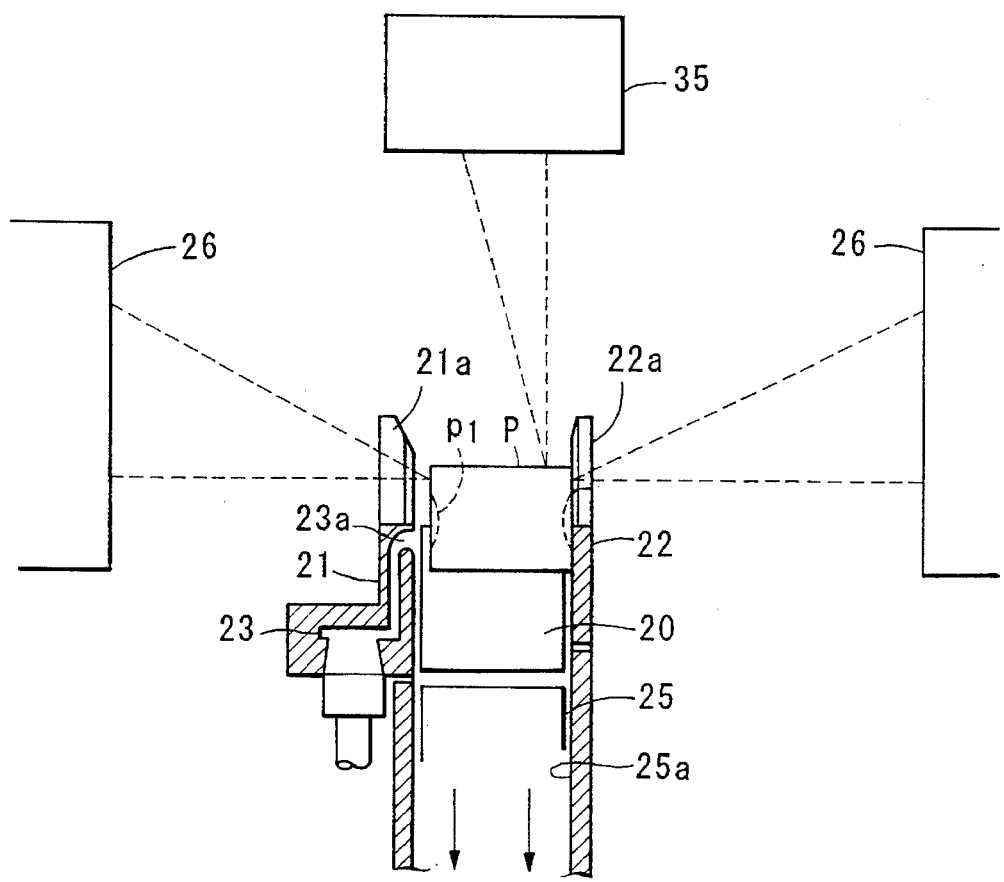
FIG. 4 is a side view of the pellet shape inspection unit shown in FIG. 3 as seen from another angle.

FIG. 4 shows a view of pellet shape inspection unit 11 from a different angle. In this Figure, a pair of side plates 21 and 22 are arranged facing each other adjacent to the end faces of roller 19 and 20. In each side plate 21 and 22, a slit (or hole) 21a and 22a is formed respectively facing an end face of pellet P placed on roller 19 from upper end to a position including the hemispherical dish p1 (or at least the length of the radius of the pellet end face).

In the interior of side plate 21 (i.e., the side plate possessing the comparatively large plate thickness) an air supply route 23 through which air supplied from an air supplying mechanism (not shown in the Figures) passes is formed; the blow-off opening 23a of this air supply route 23 opens to a position facing dish p1 of a pellet end face. This blow-off opening 23a is so formed to discharge air towards a position slightly lower than the central axis of the aforementioned end face of pellet P that the discharged air can push pellet P against the other side plate 22 (positioning surface) and the rollers 19 and 20, and in this manner, the positioning of both end faces of pellet P is achieved.

In addition, below the space formed between roller 19 and roller 20, suction device 25 and duct 25a are provided for evacuating out the air between the two side plates 21 and 22. By means of evacuating air through duct 25a using suction device 25, pellet P is pressed against rollers 19 and 20, thereby positioning the circumferential surface of pellet P.

On the exterior of each side plate 21 and 22, spot-type laser displacement sensors 26 and 26 for end face inspection are arranged facing each end face of pellet P for inspection of the respective end face. These displacement sensors 26 and 26 are driven at a high speed by means of a scanning mechanism (not shown in the Figure) in a parallel direction with respect to each pellet end face.

Figure 5:
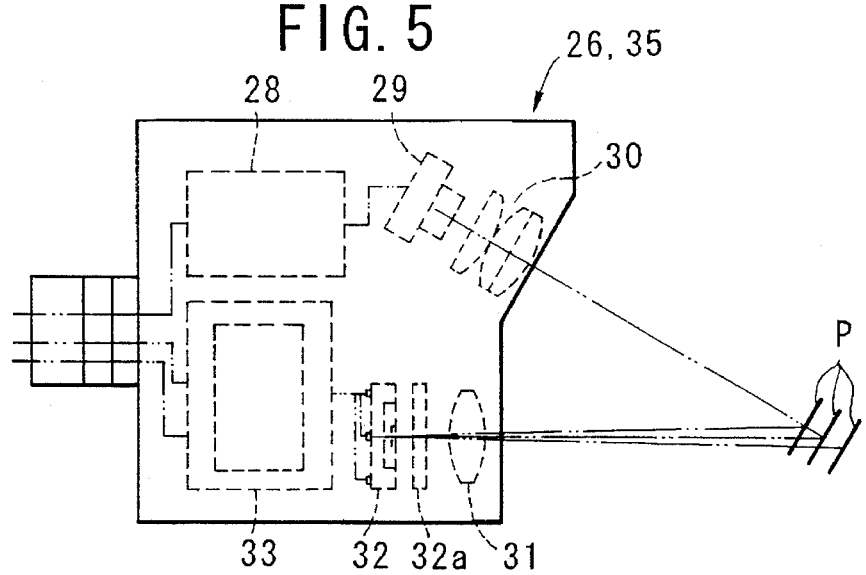
FIG. 5 is a diagram showing a structure of a laser displacement sensor.

FIG. 5 is a diagram showing a structure of this spot-type laser displacement sensor. This spot-type laser displacement sensor comprises a driving circuit 28, light source 29 which emits a laser beam through oscillation by means of the output from this driving circuit 28, lens 30 for focusing and irradiating the spot light emitted by means of light source 29 onto an end face of pellet P (surface to be inspected), light receiving lens 31 for focusing the reflected light from the surface to be inspected into spot, the spot light detecting unit 32, filter 32a arranged in front of light detecting unit 32, and signal amplifying circuit 33. As for the aforementioned light source 29, it is possible to employ a semiconductor laser, LED, or the like. As for light detecting unit 32, it is possible to employ one: linear position sensitive detector (PSD), or alternatively employ a plurality of PSD's arranged in an array. In order to avoid interference from external light, filter 32a allows the passage of only light of a predetermined wavelength which differs from the wavelength of the external light.

The position of the spot light on light detecting unit 32 changes according to deviations of the pellet surface from a standard surface, which in turn causes the output current (voltage) of light detecting unit 32 to change as well. This output is then input and amplified in signal amplifying circuit 33 as the displacement information of the surface to be inspected. In addition, light detecting unit 32 is able to detect the quantity of light from the spot light received. As a result, even when a pellet P exhibiting a poor S/N ratio of reflectivity is inspected, it is possible to obtain more precise surface information by means of combining the information relating to the quantity of incoming light and the displacement information, and then processing thereof by means of the control unit.

Figure 8:
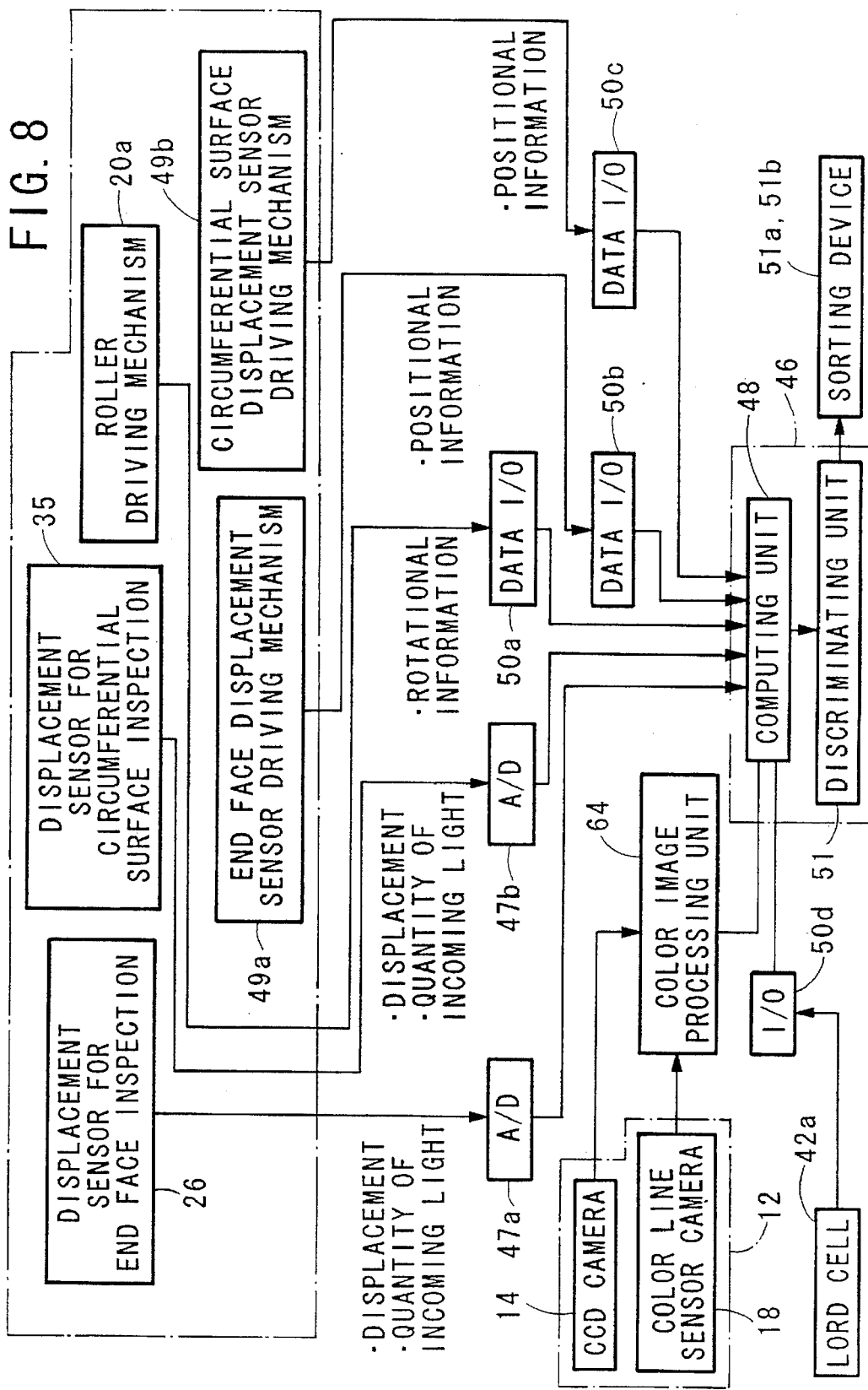
FIG. 8 is a block diagram showing a control unit of the pellet inspection apparatus.

Each displacement sensor 26 for end face inspection is designed to move in a reciprocal manner by means of driving mechanism 49a, in the radial direction of pellet P by a distance equivalent to at least the radius of pellet P (see FIG. 8). The spot light beam over this range is able to pass through slits 21a and 22a.

Consequently, by means of activating displacement sensor 26 for end face inspection in such a manner that the aforementioned spot light beam scans by a predetermined distance of an end face of pellet P, it is possible to detect the presence/absence of defects on pellet P end face by means of detecting the fluctuation of the output signal from light detecting unit 32.

In addition, as shown in FIG. 4, a spot-type laser displacement sensor possessing an identical structure to that of displacement sensor 26 for end face inspection is arranged facing the circumferential surface of pellet P as displacement sensor 35 for circumferential surface inspection, above roller 19 (see FIG. 4). This displacement sensor 35 for circumferential surface inspection is designed to move in a reciprocal by means of driving mechanism 49b by a predetermined distance in the axial direction of pellet P (see FIG. 8). In this manner, it is possible to obtain the displacement information and information regarding the quantity of incoming light of the external surface of pellet P, and hence detect any defects thereof.

Furthermore, the positional information of displacement sensors 26 for end face inspection and displacement sensor 35 for circumferential surface inspection from each respective driving means 49a and 49b, is transmitted to a control unit (to be explained hereinafter).

As shown in FIG. 2, an external surface image inspection unit 12 is provided in the forward direction of pellet shape inspection unit 11 for obtaining discoloration information of pellet P by means of picking up a color image of the external surface of pellet P (both end t aces and circumferential surface). In this external surface image inspection unit 12, a second large diameter roller 16 and a second small diameter roller 17 are provided in the forward direction of first large diameter roller 19 and first small diameter roller 20 possessing the same structures as the latter rollers. A color CCD camera 14 is arranged facing each end of pellet P supported by the aforementioned rollers (only one camera is shown in the Figures) for taking a color image of each end face.

In a state in which pellet P is placed on second large diameter roller 16 and in contact with the circumferential surface of second small diameter roller 17 being positioned in front of the former, pellet P is rotated in compliance with the rotation of the rollers 16 and 17, which, in turn, are interlocked and rotated with a predetermined peripheral speed of rotation. Above pellet P, a color line sensor camera 18 is provided to pick up a developed color circumferential surface image of a rotating pellet P through a half-mirror of the illuminating mechanism 13.

Furthermore, pellets P which are determined to be defective by means of the aforementioned visual inspection are removed by means of defective pellet sorting device 51a, while the other pellets P are subsequently sent to weight measuring unit 38.

Figure 6:
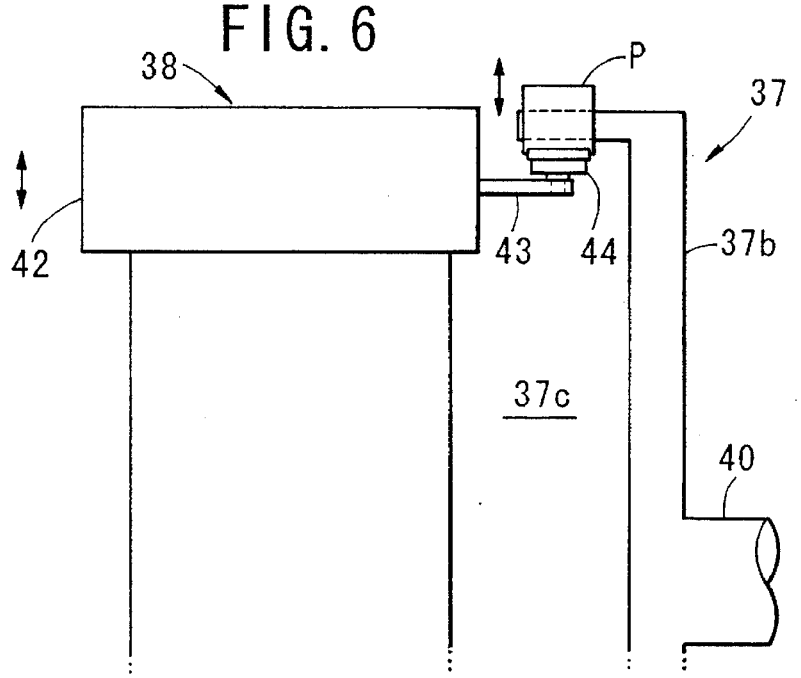
FIG. 6 is a diagram showing a structure of a pellet weight measuring unit.
Figure 7:
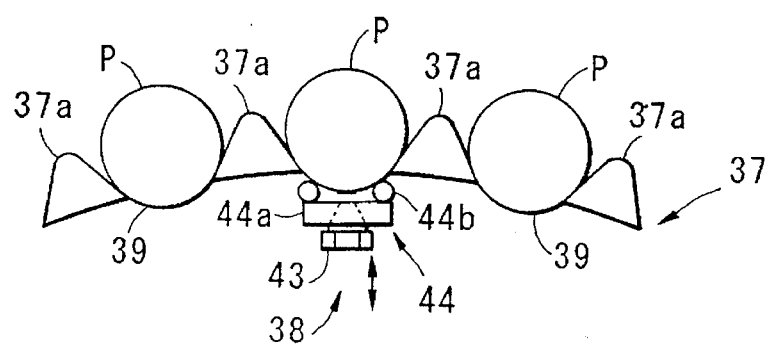
FIG. 7 is a front view of the pellet weight measuring unit shown in FIG. 6.

FIGS. 6 and 7 show a weight measuring unit 38 provided in intermittent rotating carrier disk 37 positioned in the forward (or backward) direction of external surface image inspection unit 12.

On the outer peripheral surface of carrier disk 37, teeth 37a are provided at an equal interval over the entire periphery; on the outer peripheral surface between two adjacent teeth 37a, cut-out groove 39 is formed possessing a width which is smaller than the diameter of pellet P. The transported pellet P is placed in this cut-out groove 39 and positioned by means of support from both sides using teeth 37a. In addition, in carrier disk 37, as shown in the cross sectional view of FIG. 6, driving axis 40 is formed integrally into one side surface 37b to form a circular disk, while the side surface of the opposing side forms a concavity 37c.

Near the upper part of concavity 37c, a load cell 42 for small loads is arranged such that vertical movement is possible by means of a vertical actuating mechanism (not shown in the Figures). At the end of this load cell 42, an arm 43 extending to a lower part of cut-out groove 39 is formed whereon pellet support base 44 is provided possessing a bottom member 44a fixed to an upper part of an end of arm 43 and side walls 44b on each end thereof. Carrier disk 37 is controlled in such a manner that it stops at a position where cut-out groove 39 comes to rest in the vertical direction of the aforementioned pellet support base 44 in spite of the intermittent rotation of this aforementioned carrier disk 37. During stoppage of carrier disk 37, load cell 42 is fractionally lifted by means of the aforementioned vertical actuator, thereby slightly lifting pellet P from cut-out groove 39. In this manner, it is possible to measure the weight of pellet P.

In the following, control unit 46 of pellet P inspection apparatus 5 will be explained according to the present embodiment with reference to FIG. 8.

In this Figure, the displacement information and information of the quantity of incoming light with regard to both end faces and circumferential surface of pellet P, obtained by means of displacement sensor 26 for end face inspection and displacement sensor 35 for circumferential surface inspection, are respectively converted into digital signals by means of A/D converters 47a and 47b and then input into computing unit 48. In addition, the rotational information output from driving mechanism 20a of roller 20, and the positional information of each sensor 26 and 35 output respectively from driving mechanisms 49a and 49b of displacement sensor 26 for end face inspection and displacement sensor 35 for circumferential surface inspection, are respectively input into computing unit 48 as digital signals via data I/O 50a, 50b, and 50c.

Based on the respective displacement information and information of the quantity of incoming light of the pellet P end faces and circumferential surface, computing unit 48 computes and outputs surface information and external form information of the pellet P end faces and circumferential surface, using the rotational data of pellet P and the positional data of each displacement sensor 26 and 35 as parameters.

Based on the computed results, i.e., the surface information and external form information, discriminating unit 51 extracts information such as the virtual base surface, profile of the end face and circumferential surface, presence or absence of cracks and pits, dust adhesion, bending, sagging, abnormal reflections, roundness, squareness of the end faces and circumferential surface, outer diameter, length, and the like. In particular, it is possible to determine the presence or absence of defects in pellet P by means of comparing the virtual base surfaces of the end faces and circumferential surfaces with actually detected surfaces.

The color images of both end faces and developed color image of the circumferential surface, taken by means of CCD camera 14 and color line sensor camera 18 of external surface image inspection unit 12, are respectively sent to color image processing unit 64 where surface abnormalities such as discoloration of the pellet surface are detected by means of image analysis. The detected information is subsequently sent to discriminating unit 51 via computing unit 48, and the presence or absence of surface abnormalities is determined.

The weight information by means of load cell 42a is input into computing unit 48 via I/O 50d. In computing unit 48, the volume of pellet P is obtained from the external form information of pellet P, and the density is calculated from the weight information and the volume obtained.

In discriminating unit 51, discrimination of density abnormalities of pellet P is conducted and an overall decision is made as to the pass/reject determination of pellet P based on the aforementioned. Thus, a screening inspection of pellets P is made possible in the light of a quality standard based on product specifications.

Figure 9:
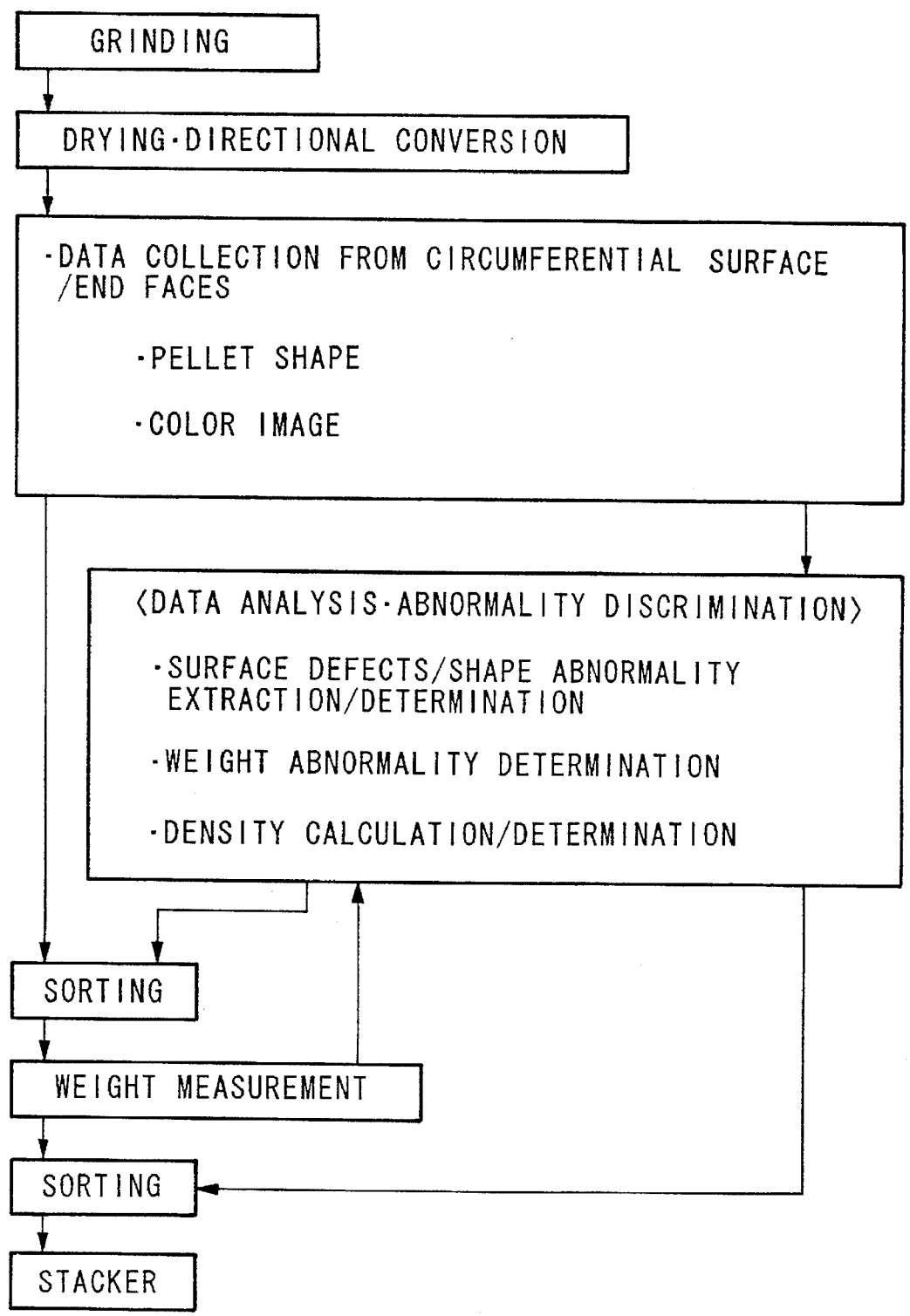
FIG. 9 is a flow chart showing an outline of a pellet inspection procedure.

In the following, the actions of the present embodiment will be explained in accordance with the pellet inspection procedure shown in FIG. 9.

The sintered pellet P is initially ground into predetermined dimensions by means of wet-type grinder 2 and sent to pellet drying/directional converter 4 where drying and directional conversion of pellet P is performed. Subsequently, the pellet P enters pellet shape inspection unit 11 and is sent between first small diameter roller 20 and first large diameter roller 19 in an intermittent manner by means of intermittent pellet supply mechanism 15. Pellet P then is placed on large diameter roller 19 serving as a base, such that a side surface thereof is supported by means of small diameter roller 20 positioned in the backward direction (see FIGS. 2 and 3). In this state, the air discharged from blow-off opening 23a of a side plate 21 blows onto dish p1 of one end face of pellet P, thereby pushing pellet P on rollers 19 and 20 in an axial direction, in such a manner that the other end face of pellet P comes in contact with the other side plate 22 (positioning base surface) (see FIG. 4). As a result, the positioning of both end faces along the axial direction is performed.

At the same time, the air between the two side plates 21 and 22 is evacuated by means of suction apparatus 25 via duct 25a, and the circumferential surface of pellet P is pushed against rollers 19 and 20 serving as the base thereof. In this manner, positioning of the circumferential surface of pellet P (radial direction) is performed.

Consequently, pellet P which is thus positioned on roller 19 and 20 serving as a base thereof is integrally rotated with the rotation of rollers 19 and 20 by means of pushing the circumferential surface thereof against rollers 19 and 20.

At this time, spot light beams are illuminated on both end faces of pellet P from the pair of displacement sensors 26 for end face inspection via slits 21a and 22a of side plates 21 and 22, respectively. The reflected light therefrom is then made to form an image on light detecting unit 32 via light receiving lens 31 and the displacement information relating to the distance from the surface to be detected is then obtained by means of the deviation of the actual image formation position from the virtual standard position (i.e., the image formation position in the case of a normal pellet) on the light detecting unit 32. Together with this, the information regarding the quantity of incoming light is also obtained from the incoming light at the image formation position.

For example, if cracks and/or dust adhesion exit in the end faces, the deviation of the image formation position increases as a result of a fluctuation of the distance up to the surface to be detected. Consequently, defects such as cracks, dust adhesion, and the like, are detectable out of the output voltage from displacement sensor 26 as the displacement information.

By means of driving mechanism 49a, the pair of displacement sensors 26 conduct a reciprocal scan by a predetermined distance at least equal to the radius of an end face of pellet P in the radial direction. In this manner, the spot light beam passes through slits 21a and 22a of side plates 21 and 22, respectively. Since the pellet P itself rotates, external inspection of the entire end face is conducted by means of reciprocal scan in the radial direction using the above-mentioned spot light.

In addition, by means of conducting a reciprocal scan of the pellet circumferential surface in the axial direction using displacement sensor 35 for circumferential surface inspection by means of driving mechanism 49b, the spot light beam similarly conducts a reciprocal scan of the pellet circumferential surface in the axial direction to produce the displacement information and information regarding the quantity of incoming light of the circumferential surface. Therefore, by rotating pellet P external inspection of the entire circumferential surface is conducted.

Figure 10:
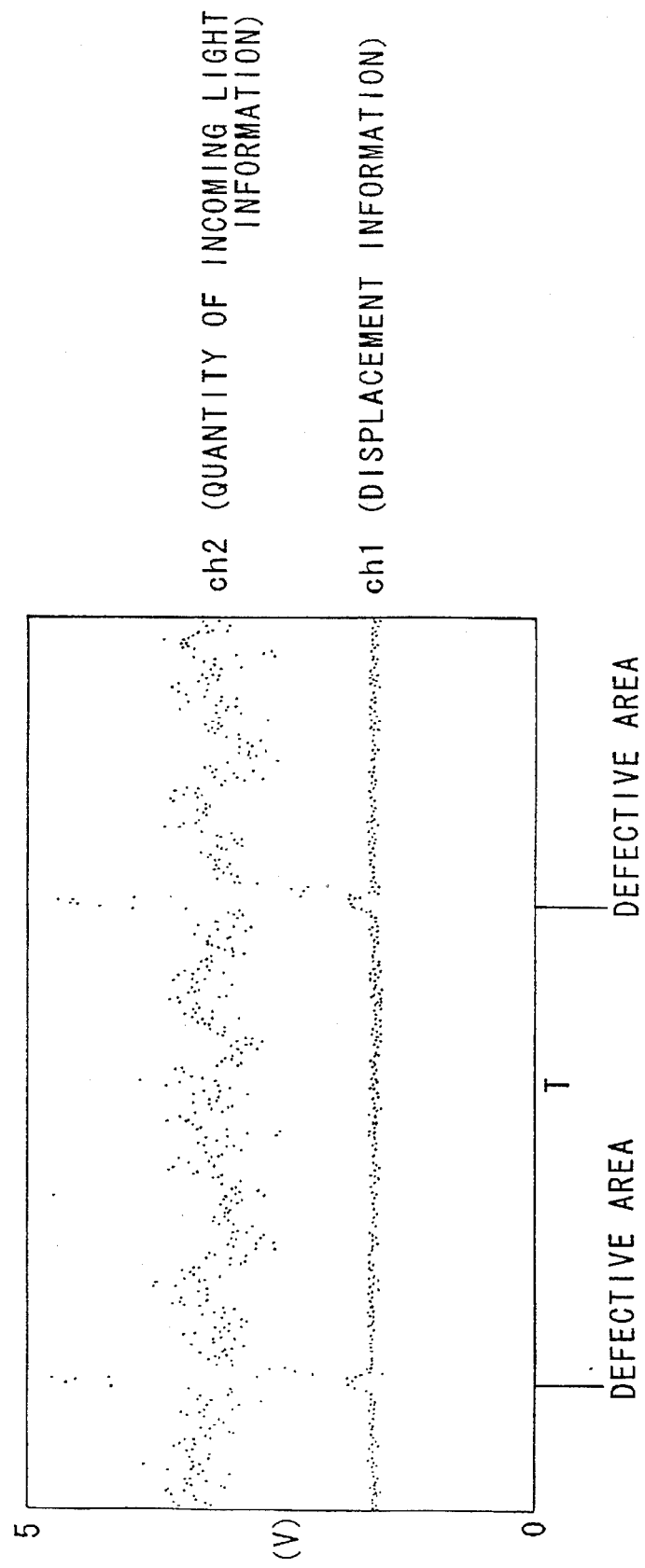
FIG. 10 is a chart showing an example of data taken by means of a displacement sensor.

The signals corresponding to the displacement and quantity of incoming light, output from the light detecting components 32 of displacement sensor 26 for end face inspection and displacement sensor 35 for circumferential surface inspection, are converted into voltage regulated by means of signal amplifying circuit 33, and then output as analogs ch1 and ch2, respectively, as shown in FIG. 10. FIG. 10 shows a portion of the data obtained by conducting end face inspection using displacement sensor 26; the horizontal axis is a time axis corresponding to the scanning position of the pellet end face. In this Figure, both ch1 and ch2 generate an abnormal voltage at defective portions.

The information regarding the displacement and quantity of incoming light of both pellet end faces and circumferential surface obtained in the aforementioned manner is then converted respectively into digital information by means of A/D converters 47a and 47b shown in FIG. 8, and input into computing unit 48 of control unit 46.

In addition, the positional information at the time of reciprocal scanning of each displacement sensor 26 and 35 is input into computing unit 48 as digital signals from respective driving mechanisms 49a and 49b. The rotational data of pellet P is input into computing unit 48 in the same manner, as a digital signal from driving mechanism 20a of rollers 19 and 20.

In computing unit 48, each respective data being input is processed, and based on the displacement information and information on the quantity of incoming light with regard to the end faces and circumferential surface of pellet P, the surface information of the displacement and quantity of incoming light with respect to each of the aforementioned, is computed using the rotational data of pellet P and the positional data of each displacement sensor 26 and 35 as parameters.

From the aforementioned resultant surface information, the virtual base surfaces of both end faces and circumferential surface are obtained by means of uniformly smoothing sections in which the displacement and quantity of incoming light temporarily fluctuate. Subsequently, in discriminating unit 51, defects of the circumferential surface and side surfaces are detected by means of the surface information of the quantity of incoming light; and with respect to defects which cannot be discriminated due to a poor S/N ratio of the pellet reflectivity of pellet P, it is possible to detect these defects by means of the supplemental use of surface information regarding the displacement. As a result, when compared with the conventional external inspection method in which only the quantity of incoming light was image processed as inspection information, it is possible to accurately and precisely detect defects by means of the present invention.

In this manner, according to the discriminating unit 51, it is possible to discriminate the profile of the circumferential surface and both end faces, defects such as cracks and pits, abnormal reflection, and/or the presence or absence of dust adhesion by means of comparing the surface information of the displacement and the quantity of incoming light to the virtual base surface. Furthermore, it is also possible to appropriately compute and output the bending of the pellet end faces, sagging, roundness, end face squareness, outer diameter dimensions, length in the axial direction, and the like.

Pellet P is then transported down into concave groove 19a of first large diameter roller 19, and a color image is then taken by means of external surface image inspection unit 12 by means of rotating pellet P in the same manner as described above between second large diameter roller 16 and second small diameter rollers 17. In this manner, the developed color image of the pellet circumferential surface taken by means of color line sensor camera 18, and the color image of both pellet end faces taken by means of CCD camera 14 are obtained. Surface abnormalities such as discoloration of the pellet surface and the like can then be discriminated by inputting the aforementioned into color image processing unit 64, extracting the characteristic points thereof, and sending these points from computing unit 48 to discriminating unit 51.

Subsequently, pellet P, which has been caught in concave groove 16a of second large diameter roller 16, is then transported by means of carrier disk 37 shown in FIGS. 6 and 7 which rotates in an intermittent manner, and the weight thereof is hence measured as described intermittent. The transported pellet P is intermittently rotated in a state in which it is placed in and supported by means of cut-out groove 39 in between two adjacent teeth 37a of carrier disk 37. When pellet P comes to rest at a position facing pellet support base 44 of weight measuring unit 38 on the upper part of carrier disk 37, load cell 42 is lifted slightly in the upward direction by means of a vertical actuating mechanism. Pellet P is subsequently raised upward by means of pellet support base 44 and supported at a position separated from cut-out groove 39. In this state, the weight of pellet P is measured by means of load cell 42.

Subsequently, when load cell 42 is returned to its initial position by means of the vertical actuating mechanism, pellet P is again supported by means of cut-out groove 39, and support base 44 then separates in the downward direction.

The weight information 42a of the measured pellet P is then input into computing unit 48. The pellet P density is then computed in computing unit 48 out of the weight information of pellet P, and the volumetric data computed based on the surface information and external form information of pellet P. By means of discriminating unit 51, pellets P with computed densities exceeding a predetermined tolerance (i.e., a predetermined allowable range) can be distinguished as density abnormalities or weight abnormalities.

In this manner, with regard to each inspected pellet P, detection of defects such as cracks and pits, the presence or absence of dust adhesion, discoloration, density abnormalities, and the like are detected by means of discriminating unit 51, and pellets which have been determined to be defective are then removed by means of defective pellet sorting devices 51a and 51b following the completion of the aforementioned inspection.

As described above, according to the present embodiment, it is possible to conduct abnormal inspection of the shape of pellet P by means of simultaneously using displacement information and information of the quantity of incoming light with regard to both pellet end faces and circumferential surface as external inspection data. In particular, when the object to be inspected is a pellet possessing a poor S/N ratio of the pellet reflectivity, even when a large number of errors exist in either the displacement information or information of the quantity of incoming light, detection misses of defects can be prevented and an accurate external inspection of the shape of pellet P can be conducted by means of the supplemental use of the other information. Furthermore, from the information regarding the quantity of incoming light, it is also possible to detect surface reflection abnormalities of the pellet surface. Additionally, it is also possible to detect surface abnormalities such as discoloration of pellet P by means of external surface imaging unit 12.

Moreover, since this external inspection can be accurately conducted at a high speed, it is possible to conduct inspection of the entire quantity of pellets P. According to the above-described inspection, it is also possible to inspect an abnormality of external forms such as the hemispherical dish surface of a pellet end face, the squareness of an end face, length, outer diameter, etc. Furthermore, by means of measuring the pellet weight using weight measuring unit 38, and computing the volume of pellet P based on the surface information and external form information of pellet P end faces and circumferential surface, it is possible to measure the density and inspect the entire quantity of pellets at a high speed for the presence or absence of density abnormalities.

In this manner, by setting up an appropriate quality standard reflecting the product specifications corresponding to measured results such as shape abnormalities, discoloration abnormalities, density abnormalities, and the like, it is possible to conduct an ideal inspection reflecting the product specifications of pellet P by means of collectively using the aforementioned measured results to form an overall decision.

Figure 11:
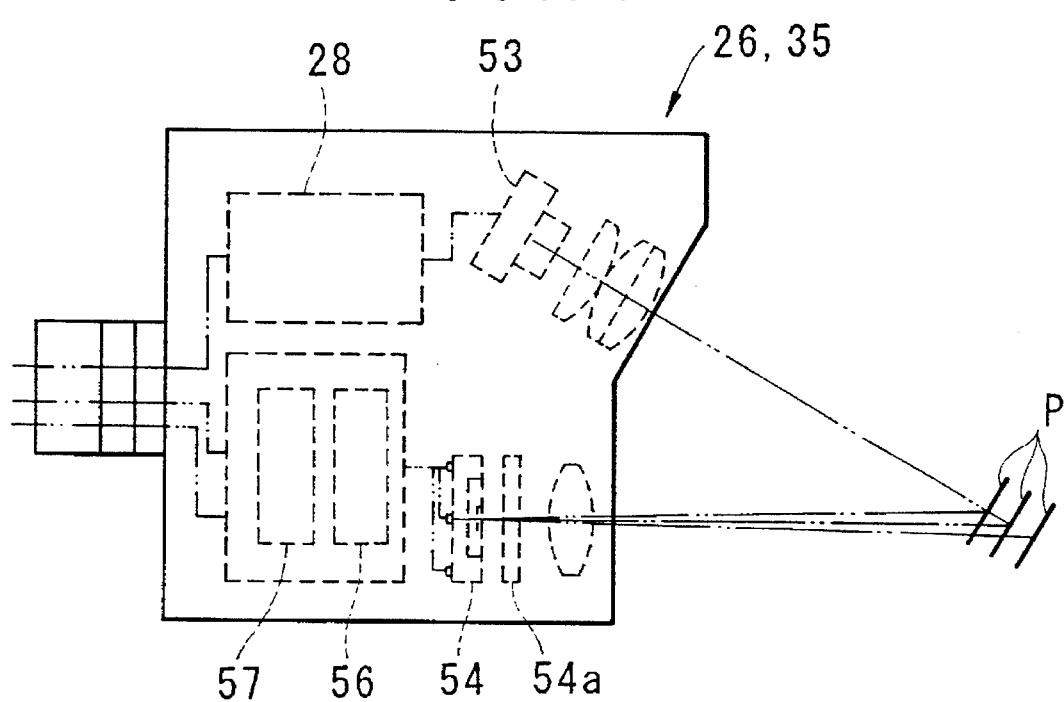
FIG. 11 is a diagram showing an internal structure of a laser displacement sensor according to a second embodiment of the present invention.
Figure 12:
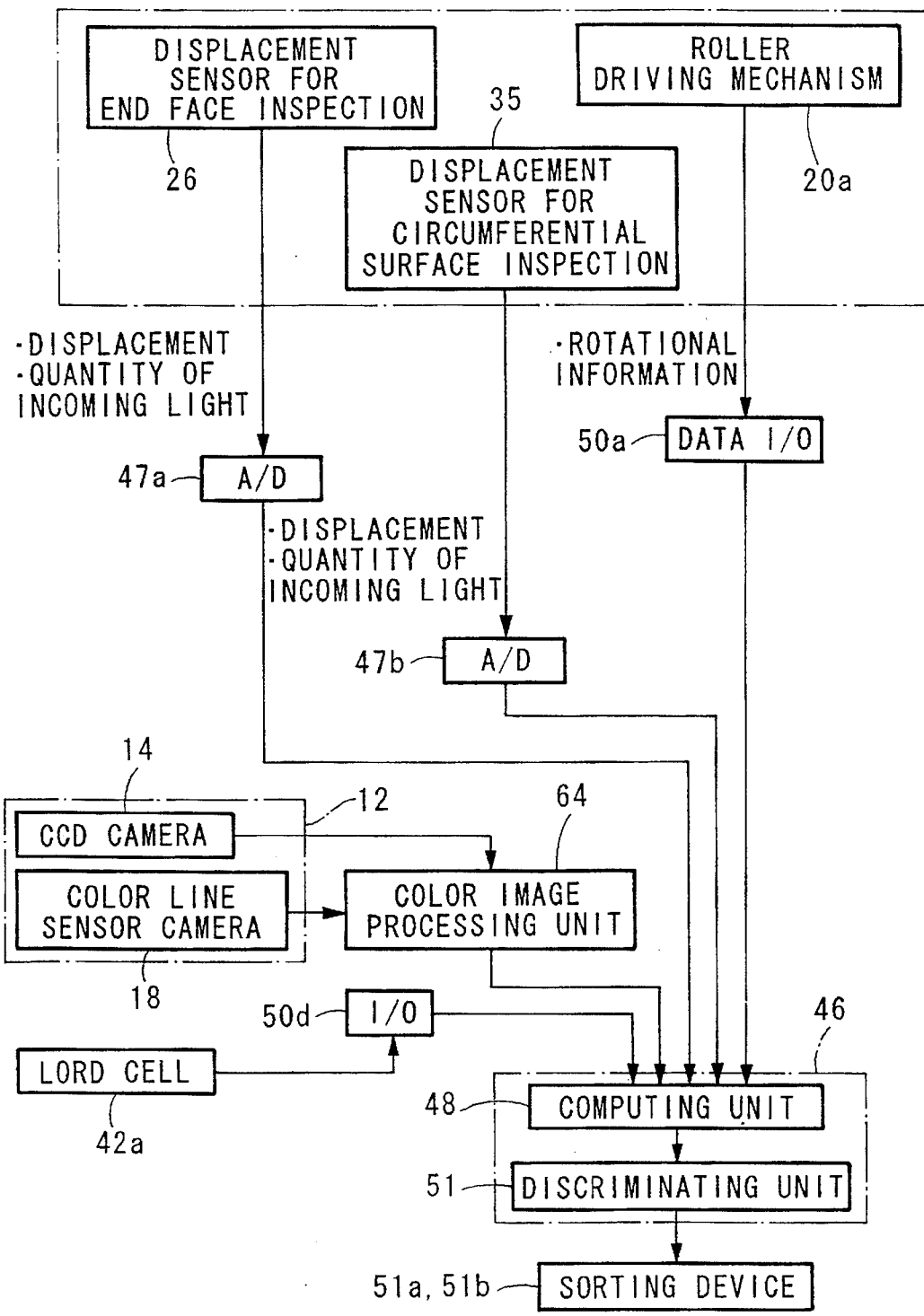
FIG. 12 is a block diagram of a control unit according to the second embodiment.

FIGS. 11 and 12 show a second embodiment of the present invention; FIG. 11 is a structural diagram of a displacement sensor, and FIG. 12 is a block diagram showing a control unit.

According to the first embodiment, a spot-type laser displacement sensor as shown in FIG. 5 is employed as the laser displacement sensor for use in displacement sensors 26 and 35 for end face inspection and circumferential surface inspection, respectively; however, it is also possible to employ a line-type laser displacement sensor (line beam emission two-dimensional camera) as shown in FIG. 11 instead. In this case, a line beam emitting laser, LED or the like is employed as light emitting unit 53, and light position sensitive detectors (PSD) arranged in an array are employed as light detecting unit 54. In light detecting unit 54, the aforementioned light position sensitive detectors are arranged in an array in an orthogonal direction to the line-focused light beam irradiated on the surface to be inspected. In addition, a filter 54a which allows passage of only light of a predetermined wavelength differing from the wavelength of the external light is provided in front of the light receiving surface of light detecting unit 54 of the above-mentioned laser displacement sensor.

In the case when a line-type displacement sensor, as described above, is employed as displacement sensors 26 and 35 for end face inspection and circumferential surface inspection, respectively, a line-focused light beam is irradiated over the entire length of each respective surface, i.e., over the entire diameter and length of both end faces and circumferential surface respectively; thus, it is unnecessary to perform a scan with each displacement sensor 26 and 35 using aforementioned driving mechanism. The line-focused light beam is then irradiated over the entire length in a direction orthogonal to the direction of rotation of each end face and circumferential surface of pellet P. Read circuit 57 for reading the displacement and quantity of incoming light is driven by means of read circuit driving mechanism 56 in the direction of the array of light detecting unit 54. In this manner, it is possible to obtain the displacement information and information regarding the quantity of incoming light over one rotation of pellet P for computing out the surface information.

In the case when a line-type displacement sensor is employed as displacement sensors 26 and 35, it is possible to use only the rotational data of pellet P as a parameter for use in developing the displacement information and information regarding the quantity of incoming light as surface information in computing mechanism 48 (see FIG. 12).

According to the second embodiment, in addition To the aforementioned effects, it is also possible to obtain the necessary information in one rotation of pellet P without the need of performing a scan using displacement sensors 26 and 35 for end face inspection and circumferential surface inspection, respectively. As a result, in addition to obtaining surface information of pellet P at an even higher speed, it is also possible to simplify the overall structure of the apparatus.

In each of the aforementioned embodiments, with regard to the spot-type or line-type laser displacement sensor for use in displacement sensor 26 for end face inspection and displacement sensor 35 for circumferential surface inspection, one position sensitive detector or an array of multiple position sensitive detectors were disposed as light detecting units 32 and 54; however, it is also possible to provide a two dimensional CCD instead. The displacement information and information regarding the quantity of incoming light is then obtained from the spot or line-focused image on this CCD.

For example, when a component irradiating a line-focused light beam is employed in a displacement sensor, the irradiated line-focused light beam forms on the CCD an image which appears as viewed from an oblique direction to the pellet surface. With regard to this two-dimensional image, data corresponding to that of one component of the array type light position sensitive detectors is contained in the incoming light brightness distribution of pixels positioned in an orthogonal direction to the line image. By inducing the incoming light position of the line-focused light beam from this incoming light brightness distribution, it is possible to measure the depth information (displacement information) of the irradiated surface to be inspected.

By recording the measured value for the depth of the line-focused light beam into the two-dimensional memory of depth information over one rotation cycle of pellet P, it is possible to then measure the developed profile (three-dimensional information) of the pellet end face and/or circumferential surface, i.e., the surface to be inspected. Consequently, it is possible to obtain both the information regarding quantity of incoming light and the displacement information by means of a two dimensional CCD. Furthermore, by matching the displacement information and information regarding the quantity of incoming light obtained from the aforementioned embodiments, as well as the surface information computed therefrom with the surface image information of pellet P, it is possible to obtain even more accurate information.

What is claimed is:

1. Cylindrical body inspection apparatus comprising:
   a) rotating means for supporting and rotating said cylindrical body;
   b) sensor comprising a light emitting means for irradiating light onto a surface to be inspected of said cylindrical body, and a light detecting means for detecting incoming light reflected from said surface to be inspected; said sensor for detecting displacement information corresponding to a displacement of distance from said surface to be inspected to said light detecting means, and information regarding quantity of incoming light corresponding to a quantity of reflected light from said surface to be inspected;
   c) computing means for computing out surface information and shape information based on said displacement information and said information regarding quantity of incoming light; and
   d) discriminating means for discriminating the presence of surface defects of said cylindrical body based on said surface information and said shape information obtained by said computing means.

2. Cylindrical body inspection apparatus according to claim 1, wherein a plurality of said sensors are provided for both opposite end faces and circumferential surface of said cylindrical body.

3. Cylindrical body inspection apparatus according to claim 1, wherein said sensor is a spot-type laser displacement sensor.

4. Cylindrical body inspection apparatus according to claim 3, wherein a scanning means is provided for conducting reciprocal scanning of said spot-type laser displacement sensor in a direction intersecting a direction of rotation of said cylindrical body.

5. Cylindrical body inspection apparatus according to claim 4, wherein rotational information of said cylindrical body from said rotating means, and positional information from said spot-type laser displacement sensor are input into said computing means; and said computing means computes out said surface information and said shape information out of said displacement information and said information regarding quantity of incoming light developed on the basis of said rotational information and said positional information.

6. Cylindrical body inspection apparatus according to claim 1, wherein said sensor is a line-type laser displacement sensor for irradiating a line-focused light beam along an entire length of said surface to be inspected of said cylindrical body.

7. Cylindrical body inspection apparatus according to claim 6, wherein rotational information of said cylindrical body from said rotating means is input into said computing means; and said computing means computes out said surface information and said shape information based on said rotational information, said displacement information and said information regarding quantity of incoming light.

8. Cylindrical body inspection apparatus according to claim 1 further comprising an end face positioning means for placing an end face of said cylindrical body into contact with a positioning surface in a rotatable manner, and circumferential surface positioning means for placing said circumferential surface of said cylindrical body into contact with a positioning surface in a rotatable manner.

9. Cylindrical body inspection apparatus according to claim 1 further comprising:
   image pickup means for picking up color images of both said opposite end faces and said circumferential surface of said cylindrical body;
   discoloration computing means for computing out discoloration information of a surface of said cylindrical body based on said color images; and
   discoloration discriminating means for discriminating presence of discoloration abnormalities of said cylindrical body based on said discoloration information.

10. Cylindrical body inspection apparatus according to claim 1, wherein said light receiving means is selected from the group consisting of one position sensitive detector, a plurality of position sensitive detectors arranged in an array, and a two-dimensional charge coupled device.

11. Cylindrical body inspection apparatus according to claim 1, further comprising weight measuring means for measuring the weight of each cylindrical body and generating weight information of the cylindrical body, and wherein said computing means computes the density of the cylindrical body using said weight information, said surface information and said shape information, of the cylindrical body.

* * * * *